(12) United States Patent
Lecalve

(10) Patent No.: US 6,517,584 B1
(45) Date of Patent: Feb. 11, 2003

(54) FLEXIBLE PROSTHESIS IN PARTICULAR FOR CURING HERNIAS BY COLIOSCOPY

(75) Inventor: Jean-Luc Lecalve, Rennes (FR)

(73) Assignee: Ethicon, Issy-les-Moulineaux (FR)

( * ) Notice: Subject to any disclaimer, the term of this patent is extended or adjusted under 35 U.S.C. 154(b) by 0 days.

(21) Appl. No.: 09/701,575
(22) PCT Filed: Apr. 5, 2000
(86) PCT No.: PCT/FR00/00845
§ 371 (c)(1), (2), (4) Date: Feb. 5, 2001
(87) PCT Pub. No.: WO00/61033
PCT Pub. Date: Oct. 19, 2000

(30) Foreign Application Priority Data

Apr. 8, 1999 (FR) .............................. 99 04390

(51) Int. Cl.[7] .................................. A61F 2/02
(52) U.S. Cl. ................... 623/23.72; 623/23.74
(58) Field of Search ........................ 623/11.11, 23.72, 623/1.13, 1.14, 1.18, 1.19, 1.36, 23.74; 606/139, 151, 155, 157, 224, 225, 78

(56) References Cited

U.S. PATENT DOCUMENTS

| 3,810,467 A | | 5/1974 | Frankenthal | 128/95 |
|---|---|---|---|---|
| 4,485,816 A | * | 12/1984 | Krumme | 606/78 |
| 5,002,563 A | * | 3/1991 | Pyka et al. | 606/222 |
| 5,219,358 A | * | 6/1993 | Bendel et al. | 606/78 |
| 5,333,624 A | | 8/1994 | Tovey | 128/897 |
| 5,456,720 A | * | 10/1995 | Schultz et al. | 623/12 |
| 5,586,983 A | * | 12/1996 | Sanders et al. | 606/61 |
| 5,810,851 A | | 9/1998 | Yoon | 606/148 |
| 5,824,082 A | * | 10/1998 | Brown | 623/11.11 |
| 5,972,022 A | * | 10/1999 | Huxel | 606/215 |
| 5,989,268 A | * | 11/1999 | Pugsley, Jr. et al. | 606/144 |
| 6,042,592 A | * | 3/2000 | Schmitt | 606/151 |
| 6,113,611 A | * | 9/2000 | Allen et al. | 606/151 |

FOREIGN PATENT DOCUMENTS

| DE | 197 11 288 | | 10/1998 | |
| FR | 2 710 518 | | 4/1995 | |
| FR | WO 96/41588 | * | 12/1996 | A61F/2/00 |
| FR | 2 789 888 A1 | * | 8/2000 | A61F/2/02 |

* cited by examiner

*Primary Examiner*—David H. Willse
*Assistant Examiner*—Javier G. Blanco
(74) *Attorney, Agent, or Firm*—Jacobson Holman PLLC

(57) ABSTRACT

A flexible prosthesis, in particular for curing hernias by colioscopy, the prosthesis including at least one anchor, device made of shape memory material designed to be deformed merely under temperature control from a storage position into a fixing position in which the anchor device interferes with the surrounding tissue.

55 Claims, 1 Drawing Sheet

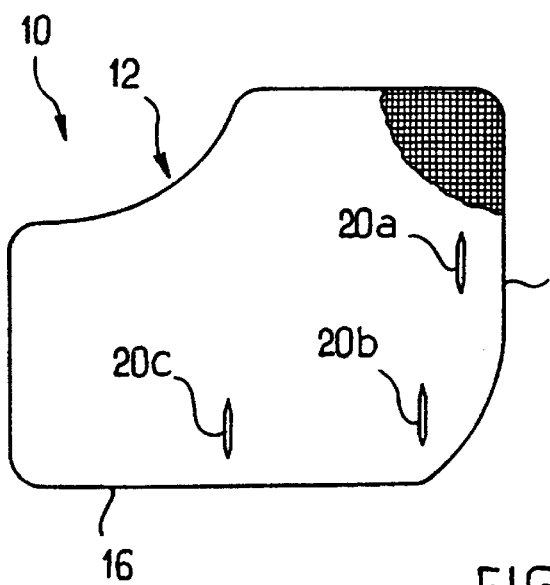
FIG_1
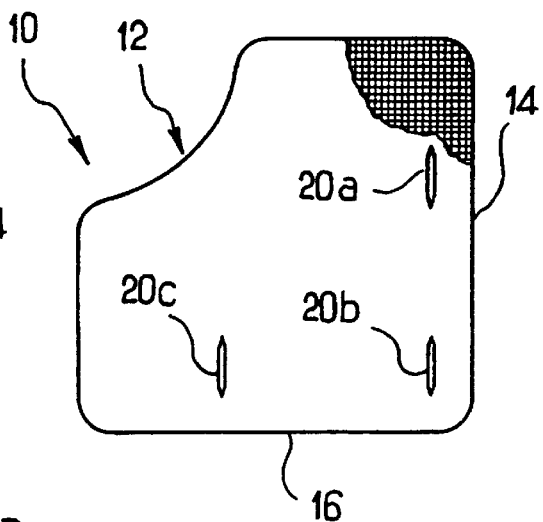
FIG_2
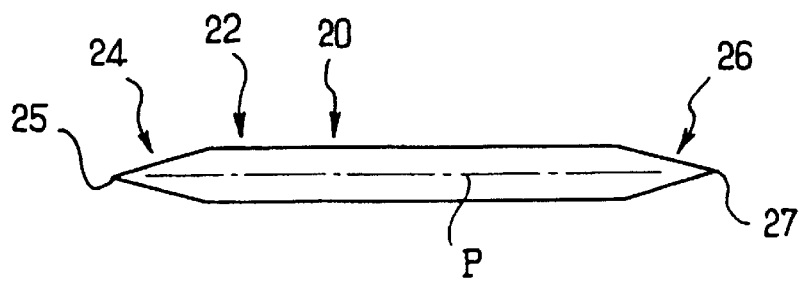
FIG_3
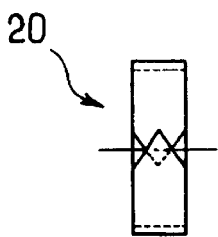
FIG_4
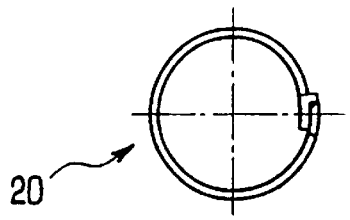
FIG_5

FLEXIBLE PROSTHESIS IN PARTICULAR FOR CURING HERNIAS BY COLIOSCOPY

BACKGROUND OF THE INVENTION

1. Field of the Invention

The present invention relates to the field of prostheses made of flexible cloth.

It applies in particular to prostheses designed to be into place by endoscopic surgery.

More precisely still, the present invention applies preferably to fixing the flexible prostheses defined in document FR-A-2 710 518. The means defined in that document are designed mainly for curing hernias by colioscopy using a precut web which is put into place by laparoscopy.

2. Description of the Related Art

Generally, flexible cloth prostheses are fixed by staples or by stitches.

Stapling is quite easy to perform in most open operations. It is more difficult when operating by colioscopy. In all cases it is rather expensive.

The fixing of flexible prostheses by stitches is cheaper, but more difficult to perform, particularly for colioscope type interventions.

In the context of the device described in above-mentioned document FR-A-2 710 518, for example, it is recommended to perform peritonization with a needle using 10 cm to 15 cm resorbable thread that is locked every 3 or 4 stitches by a clamp.

Proposals have indeed been made to eliminate the drawbacks of the prior art by having recourse to biological adhesives; however to the knowledge of the Applicant, those attempts have not yet given satisfaction.

SUMMARY OF THE INVENTION

An object of the present invention is thus to propose a novel device making it possible to eliminate the drawbacks of the prior art by facilitating the fixing of flexible prostheses on a member of the living body.

In the context of the present invention, this object is achieved by a flexible prosthesis comprising at least one anchor device (20) made of a material having shape memory and designed to be deformed merely by temperature control, to go from a storage position in which the device (20) is at least substantially rectilinear and adjacent to the prosthesis (10) to a fixing position in which said anchor device (20) is generally in the form of a loop projecting considerably from the prosthesis (10) so as to penetrate into the surrounding tissue.

According to another advantageous characteristic of the present invention, said prosthesis includes a plurality of anchor devices that are mutually parallel in the initial, storage position.

BRIEF DESCRIPTION OF THE DRAWINGS

Other characteristics, objects, and advantages of the present invention will appear on reading the following detailed description and from the accompanying drawing, given by way of non-limiting example, and in which:

FIGS. 1 and 2 are two diagrammatic views of flexible prostheses fitted with anchor devices of the present invention;

FIG. 3 is a side view of an anchor device of the present invention, shown in its initial, storage position; and FIGS. 4 and 5 are two mutually orthogonal lateral views showing the same device in its fixing position.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The invention applies to any type of flexible prosthesis.

Nevertheless, it applies most particularly to prostheses 10 of the type shown in accompanying FIGS. 1 to 2, designed to be put into place using a device of the type described in document FR-A-2 710 518.

Such prostheses 10 are designed to cure hernias, and are generally rectangular in outline with rounded corners. They also have a cutout 12 in their infero-lateral corners for fitting to the bulge of the psoas.

They are packaged in the flat state in a blister pack and they are associated with fork-shaped means designed to roll up said prostheses at the time they are used. Once rolled up, the prostheses are moved to the site at which they are to be put into place by means of a trocar.

As mentioned above, in the context of the present invention, the prosthesis 10 is fitted with at least one anchor device 20 made of a shape memory material designed to deform merely under temperature control, so as to go from a storage position to a fixing position in which said anchor device 20 interferes with the surrounding tissue.

Still more precisely, in accordance with the present invention, the anchor device 20 is preferably designed to deform merely under temperature control, so as to go from a storage position as shown in FIG. 3 in which the device 20 is at least substantially rectilinear and adjacent to the prosthesis 10, to a fixing position as shown in FIGS. 4 and 5 in which the device 20 is generally in the form of a loop that projects to a large extent from the prosthesis so as to penetrate into the surrounding tissue.

The anchor device 20 is preferably made out of a TiNi memory alloy.

At rest, prior to deforming, it is preferably in the form of a rectilinear bar 22 of rectangular right section with ends 24 and 26 that taper in a chamfer.

The V-shaped ends 24 and 26 thus define respective points 25 and 27 situated in the longitudinal plane of symmetry P of the anchor device 20.

By way of non-limiting example:

the total length of the device 20 is about 18 mm;

the width of the device 20 is about 1.62 mm;

the thickness of the device 20 is about 0.25 mm; and the angle at the end points of the device 20 is about 30.

The device 20 is also placed on the prosthesis in a direction that extends parallel to the axis about which the prosthesis 10 is rolled up.

Still more precisely, in the context of the present invention, said prosthesis 10 preferably has a plurality of anchor devices 20 that are mutually parallel in the initial, storage position. These various anchor devices 20 are also parallel to the axis about which the prosthesis 10 is rolled up.

Thus, in the context of the present invention, the prosthesis preferably has three anchor devices 20 Generally disposed in respective corners of the prosthesis 10 other than the corner that has the cutout 12.

Still more precisely, as can be seen in accompanying FIGS. 1 and 2, two of the anchor devices referenced 20a and 20b preferably have their longitudinal axes substantially in alignment parallel to one of the edges 14 to the prosthesis, while the mutually parallel anchor devices 20b and 20c have their longitudinal axes perpendicular to another edge 16 of the prosthesis 10 extending perpendicularly to the above-mentioned edge 14, with the two last-mentioned anchor devices 20b and 20c being situated at substantially the same distance from said other edge 16.

The anchor device 20 is initially secured to the prosthesis 10 merely by threading the device 20 through the mesh of the web constituting the prosthesis 10.

In order to use the prosthesis of the present invention, it suffices, once said prosthesis 10 has been brought to its site of use, deployed, and put into position, to heat the anchor devices 20 by any appropriate means, e.g. by means of a conventional thermal scalpel, so as to deform the anchor devices into their fixing position as shown in FIGS. 4 and 5, where the devices penetrate into the surrounding tissue.

In this fixing position, the anchor devices 20 are in the form of closed circular loops having a mean diameter of about 5 mm.

The Applicant has observed that the sharp ends of the anchor device 20 enable it to become implanted in satisfactory manner in tissue without requiring backing or an anvil as is required for conventional staples. The shape of anchor devices 20 of the present invention makes it possible to achieve progressive deformation from an original rectilinear state to a curvilinear state in the fixing position, with the ends of the anchor devices penetrating progressively into the adjacent tissue.

The prosthesis 10 must be made of a material that is insensitive to the temperature at which the shape memory material constituting the anchor devices 20 reacts. In this context, the prosthesis 10 is preferably constituted as a knit based on a non-resorbable synthetic monofilament constituted by an isotactic stereo-isomer of polypropylene, e.g. having the formula $(C_3H_6)_n$.

The present invention thus enables the prosthesis 10 to be fixed much more easily than with any of the fixing means that have been proposed in the past.

Naturally, the present invention is not limited to the particular embodiment described above, and it extends to any variant within the spirit of the invention.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A flexible prosthesis comprising at least one anchor device made of shape memory material designed to be deformed under temperature control from a storage position in which said anchor device is at least substantially rectilinear and adjacent to the prosthesis to a fixing position in which said anchor device is generally in the form of a loop projecting considerably from the prosthesis so as to penetrate into surrounding tissue, each anchor device being placed on the prosthesis in a direction that is substantially parallel to an axis about which the prosthesis is rolled up.

2. The prosthesis according to claim 1, further comprising a plurality of anchor devices that are mutually parallel in said storage position.

3. The prosthesis according to claim 1, wherein said anchor device is made of a memory TiNi alloy.

4. The prosthesis according to claim 1, wherein said anchor device when at rest, prior to deformation, is in the form of a rectilinear strip of rectangular cross-section having ends which taper in chamfers.

5. The prosthesis according to claim 4, wherein the ends of the anchor device are V-shaped and define respective points situated in a longitudinal plane of symmetry of said anchor device.

6. The prosthesis according to claim 4, wherein an angle of said tapered ends of the anchor device is about 30°.

7. The prosthesis according to claim 1, wherein a total length of the anchor device is about 18 mm.

8. The prosthesis according to claim 1, wherein a width of the anchor device is about 1.62 mm.

9. The prosthesis according to claim 1, wherein a thickness of the anchor device is about 0.25 mm.

10. The prosthesis according to claim 1, wherein said prosthesis includes three anchor devices.

11. The prosthesis according to claim 10, wherein said three anchor devices are disposed in a vicinity of three respective corners of said prosthesis.

12. The prosthesis according to claim 1, said prosthesis having a generally rectangular outline with rounded corners and a cutout in an infero-lateral corner that fits over a bulge of a psoas.

13. The prosthesis according to claim 12, wherein each of said rounded corners, excluding said infero-lateral corner, has an anchor device generally disposed therein.

14. The prosthesis according to claim 1, further comprising a first anchor device, a second anchor device and a third anchor device, said first and second anchor devices having longitudinal axes that are substantially in alignment parallel to an edge of the prosthesis, and said second and third anchor devices being mutually parallel and having longitudinal axes that are perpendicular to another edge of the prosthesis and which are situated at substantially a same distance from said another edge.

15. The prosthesis according to claim 1, wherein said anchor device is initially secured to the prosthesis by being interlaced through a web mesh constituting the prosthesis.

16. The prosthesis according to claim 1, wherein a shape of the anchor device in the fixing position is that of a closed circular loop.

17. The prosthesis according to claim 16, wherein said closed circular loop has a mean diameter of about 5 mm.

18. The prosthesis according to claim 1, wherein said prosthesis made of a material that is insensitive to a response temperature of the shape memory material constituting the anchor device.

19. The prosthesis according to claim 1, wherein said prosthesis is constituted by a knit based on a non-resorbable synthetic monofilament constituted by an isostatic stereo-isomer of polypropylene.

20. A flexible prosthesis comprising at least one anchor device made of shape memory material designed to be deformed under temperature control from a storage position in which said anchor device is at least substantially rectilinear and adjacent to the prosthesis to a fixing position in which said anchor device is generally in the form of a loop projecting considerably from the prosthesis so as to penetrate into surrounding tissue, said prosthesis having a generally rectangular outline with rounded corners and a cutout in an infero-lateral corner that fits over a bulge of a psoas.

21. The prosthesis according to claim 20, further comprising a plurality of anchor devices that are mutually parallel in said storage position.

22. The prosthesis according to claim 20, wherein said anchor device is made of a memory TiNi alloy.

23. The prosthesis according to claim 20, wherein said anchor device when at rest, prior to deformation, is in the form of a rectilinear strip of rectangular cross-section having ends which taper in chamfers.

24. The prosthesis according to claim 23, wherein the ends of the anchor device are V-shaped and define respective points situated in a longitudinal plane of symmetry of said anchor device.

25. The prosthesis according to claim 20, wherein a total length of the anchor device is about 18 mm.

26. The prosthesis according to claim 20, wherein a width of the anchor device is about 1.62 mm.

27. The prosthesis according to claim 20, wherein a thickness of the anchor device is about 0.25 mm.

28. The prosthesis according to claim 20, wherein an angle of said tapered ends of the anchor device is about 30°.

29. The prosthesis according to claim 20, wherein each anchor device is placed on the prosthesis in a direction that is substantially parallel to an axis about which the prosthesis is rolled up.

30. The prosthesis according to claim 20, wherein said prosthesis includes three anchor devices.

31. The prosthesis according to claim 20, wherein said three anchor devices are disposed in a vicinity of three respective corners of said prosthesis.

32. The prosthesis according to claim 20, wherein each of said rounded corners, excluding said infero-lateral corner, has an anchor device generally disposed therein.

33. The prosthesis according to claim 20, further comprising a first anchor device, a second anchor device and a third anchor device, said first and second anchor devices having longitudinal axes that are substantially in alignment parallel to an edge of the prosthesis, and said second and third anchor devices being mutually parallel and having longitudinal axes that are perpendicular to another edge of the prosthesis and which are situated at substantially a same distance from said another edge.

34. The prosthesis according to claim 20, wherein said anchor device is initially secured to the prosthesis by being interlaced through a web mesh constituting the prosthesis.

35. The prosthesis according to claim 20, wherein a shape of the anchor device in the fixing position is that of a closed circular loop.

36. The prosthesis according to claim 20, wherein said closed circular loop has a mean diameter of about 5 mm.

37. The prosthesis according to claim 20, wherein said prosthesis is made of a material that is insensitive to a response temperature of the shape memory material constituting the anchor device.

38. The prosthesis according to claim 20, wherein said prosthesis is constituted by a knit based on a non-resorbable synthetic monofilament constituted by an isostatic stereoisomer of polypropylene.

39. A flexible prosthesis comprising a first anchor device, a second anchor device and a third anchor device, said first and second anchor devices having longitudinal axes that are substantially in alignment parallel to an edge of the prosthesis, and said second and third anchor devices being mutually parallel and having longitudinal axes that are perpendicular to another edge of the prosthesis and which are situated at substantially a same distance from said another edge, each of said anchor devices made of shape memory material designed to be deformed under temperature control from a storage position in which each of said anchor devices is at least substantially rectilinear and adjacent to the prosthesis to a fixing position in which each of said anchor devices is generally in the form of a loop projecting considerably from the prosthesis so as to penetrate into surrounding tissue.

40. The prosthesis according to claim 39, wherein said anchor devices are made of a memory TiNi alloy.

41. The prosthesis according to claim 39, wherein each of said anchor devices, when at rest prior to deformation, is in the form of a rectilinear strip of rectangular cross-section having ends which taper in chamfers.

42. The prosthesis according to claim 41, wherein the ends of said anchor devices are V-shaped and define respective points situated in a longitudinal plane of symmetry of said anchor devices.

43. The prosthesis according to claim 39, wherein a total length of each anchor device is about 18 mm.

44. The prosthesis according to claim 39, wherein a width of each anchor device is about 1.62 mm.

45. The prosthesis according to claim 39, wherein a thickness of each anchor device is about 0.25 mm.

46. The prosthesis according to claim 39, wherein an angle of said tapered ends of said anchor devices is about 30°.

47. The prosthesis according to claim 39, wherein each anchor device is placed on the prosthesis in a direction that is parallel to an axis about which the prosthesis is rolled up.

48. The prosthesis according to claim 39, wherein said three anchor devices are disposed in a vicinity of three respective corners of said prosthesis.

49. The prosthesis according to claim 39, said prosthesis having a generally rectangular outline with rounded corners and a cutout in an infero-lateral corner that fits over a bulge of a psoas.

50. The prosthesis according to claim 49, wherein each of said rounded corners, excluding said infero-lateral corner, has one of said first, second and third anchor devices generally disposed therein.

51. The prosthesis according to claim 39, wherein each of said anchor devices is initially secured to the prosthesis by being interlaced through a web mesh constituting the prosthesis.

52. The prosthesis according to claim 39, wherein a shape of each of said anchor devices in the fixing position is that of a closed circular loop.

53. The prosthesis according to claim 52, wherein said closed circular loop has a mean diameter of about 5 mm.

54. The prosthesis according to claim 39, wherein said prosthesis is made of a material that is insensitive to a response temperature of the shape memory material constituting the anchor devices.

55. The prosthesis according to claim 39, wherein said prosthesis is constituted by a knit based on a non-resorbable synthetic monofilament constituted by an isostatic stereoisomer of polypropylene.

* * * * *